US011406580B2

(12) United States Patent
Sabelle et al.

(10) Patent No.: US 11,406,580 B2
(45) Date of Patent: Aug. 9, 2022

(54) USE OF DIHYDROISOQUINOLINIUM SALTS FOR TREATING KERATIN MATERIALS, COMPOSITIONS AND IMPLEMENTATION PROCESSES

(71) Applicant: L'OREAL, Paris (FR)

(72) Inventors: Stéphane Sabelle, Aulnay-sous-Bois (FR); Aziz Fadli, Aulnay-sous-Bois (FR); Alexandra Charrier, Aulnay-sous-bois (FR)

(73) Assignee: L'OREAL, Paris (FR)

( * ) Notice: Subject to any disclaimer, the term of this patent is extended or adjusted under 35 U.S.C. 154(b) by 191 days.

(21) Appl. No.: 16/064,256

(22) PCT Filed: Dec. 23, 2016

(86) PCT No.: PCT/EP2016/082577
§ 371 (c)(1),
(2) Date: Jun. 20, 2018

(87) PCT Pub. No.: WO2017/109183
PCT Pub. Date: Jun. 29, 2017

(65) Prior Publication Data
US 2019/0008741 A1 Jan. 10, 2019

(30) Foreign Application Priority Data
Dec. 23, 2015 (FR) ...................................... 1563273

(51) Int. Cl.
| | | |
|---|---|---|
| *A61K 8/49* | (2006.01) | |
| *C07D 217/04* | (2006.01) | |
| *A61K 8/22* | (2006.01) | |
| *A61Q 5/08* | (2006.01) | |
| *C07D 401/06* | (2006.01) | |

(52) U.S. Cl.
CPC .............. *A61K 8/4926* (2013.01); *A61K 8/22* (2013.01); *A61K 8/4946* (2013.01); *A61Q 5/08* (2013.01); *C07D 217/04* (2013.01); *C07D 401/06* (2013.01)

(58) Field of Classification Search
CPC ...... C09D 175/06; C09D 5/08; C09D 175/04; C08G 18/246; C08G 18/42; C08G 18/622; C08G 18/715; C08G 2150/90; C08G 18/6225; C08G 18/423; C08G 18/4676; C08G 18/792; C08G 18/711; C08L 75/00
See application file for complete search history.

(56) References Cited

U.S. PATENT DOCUMENTS

| | | |
|---|---|---|
| 2006/0156488 A1 | 7/2006 | David et al. |
| 2011/0056508 A1 | 3/2011 | Gross et al. |
| 2011/0146005 A1 | 6/2011 | Gross et al. |

FOREIGN PATENT DOCUMENTS

| | | |
|---|---|---|
| EP | 1672033 A2 | 6/2006 |
| GB | 1125619 A | 8/1968 |
| WO | 01/16273 A1 | 3/2001 |
| WO | 2008/025240 A1 | 3/2008 |
| WO | 2009/043613 A1 | 4/2009 |
| WO | 2017/109184 A1 | 6/2017 |
| WO | 2017/109185 A1 | 6/2017 |

OTHER PUBLICATIONS

Non-Final Office Action for copending U.S. Appl. No. 16/064,291, dated Jun. 18, 2020.
International Search Report for Application No. PCT/EP2016/082577, dated May 11, 2017.
Non-Final Office Action for co-pending U.S. Appl. No. 16/064,291, dated Mar. 22, 2019.
International Search Report for counterpart Application No. PCT/EP2016/082578, dated Feb. 22, 2017.
International Search Report for counterpart Application No. PCT/EP2016/082580, dated Mar. 6, 2017.
Cannon, et al., "Polyphosphoric Acid in the Bischler-Napieralski Reaction," Journal of the American Pharmaceutical Association, Scientific Edition A8, XP009190223, vol. 47, 1958, pp. 353-355.
Copp, F.C. et al., "Two New Short-Acting Nondepolarizing Neuromusclar Blocking Agents," Experientia, Springer Basel AG, CH, vol. 28, No. 1, Jan. 1, 1972, pp. 47-48.
Hughes, R., "Evaluation of the Neuromuscular Blocking Properties and Side-Effects of the Two New Isoquinolinium Bisquaternary Compounds (BW.252C64 and BW.403C65)," British Journal of Anaesthesia, vol. 44, No. 27, Jan. 1, 1972, pp. 27-42.
Stenlake, John B. et al., "Bis-3, 4-Dihydroisoquinolinium Salts as Potential Neuromuscular Blocking Agents," Chimica Therapeutique, Editions Dimeo, Arcueil, Fr, vol. 16, No. 6, Jan. 1, 1981, pp. 503-507.

(Continued)

*Primary Examiner* — Matthew P Coughlin
*Assistant Examiner* — Thurman Wheeler
(74) *Attorney, Agent, or Firm* — The Marbury Law Group, PLLC

(57) ABSTRACT

Use of dihydroisoquinolinium salts for treating keratin materials, compositions and implementation processes The present invention relates to the use of one or more dihydroisoquinolinium salts for treating keratin materials, in particular keratin fibres, especially human keratin fibres such as the hair. The invention also relates to a process for treating keratin materials using said salts and optionally in the presence of one or more chemical oxidizing agents. A subject of the invention is also a composition for lightening keratin materials, comprising one or more dihydroisoquinolinium salts as defined below and one or more chemical oxidizing agents.

11 Claims, No Drawings

(56) References Cited

OTHER PUBLICATIONS

Szántay, Csaba et al., "Beiträge zur Chemie der Heterocyclishchen, Pseudobasischen Aminocarbinole, XXV. Redoxprozesse bei aus Bis-[3.4-dihydro-isochinolinium]-Salzen freisetzbaren Basen," Chemische Berichte, vol. 96, No. 7, Jul. 1, 1963, p. 1779-1787 (translation not available).
Final Office Action for co-pending U.S. Appl. No. 16/064,291, dated Sep. 3, 2019.
Non-Final Office Action for copending U.S. Appl. No. 16/064,129, dated Dec. 3, 2020.
Non-Final Office Action for copending U.S. Appl. No. 16/064,291, dated Dec. 10, 2020.
Final Office Action for copending U.S. Appl. No. 16/064,129, dated Jun. 14, 2021.
Non-Final Office Action for copending U.S. Appl. No. 16/064,129, dated Dec. 24, 2021.

USE OF DIHYDROISOQUINOLINIUM SALTS FOR TREATING KERATIN MATERIALS, COMPOSITIONS AND IMPLEMENTATION PROCESSES

CROSS REFERENCE TO RELATED APPLICATIONS

This is a national stage application of PCT/EP2016/082577, filed internationally on Dec. 23, 2016, which claims priority to French Application No. 1563273 filed on Dec. 23, 2015, both of which are incorporated by reference herein in their entireties.

The present invention relates to the use of one or more dihydroisoquinolinium salts for treating keratin materials, in particular keratin fibres, especially human keratin fibres such as the hair. The invention also relates to a process for treating keratin materials using said salts and optionally in the presence of one or more chemical oxidizing agents.

A subject of the invention is also a composition for lightening keratin materials, comprising one or more dihydroisoquinolinium salts as defined below and one or more chemical oxidizing agents.

The present invention also relates to one or more particular dihydroisoquinolinium salts and also to compositions containing them, in particular compositions comprising a physiologically acceptable medium.

When a person wishes to change hair colour, in particular when she wishes to obtain a colour lighter than her original colour, it is often necessary to perform lightening or bleaching of the hair. To do this, lightening or bleaching products are used. This step is optionally combined with a hair colouring step.

It is known practice to lighten or bleach keratin materials, especially keratin fibres, and in particular human keratin fibres such as the hair, with lightening or bleaching compositions containing one or more chemical oxidizing agents.

Among the chemical oxidizing agents used conventionally, mention may be made of hydrogen peroxide, compounds that can produce hydrogen peroxide by hydrolysis, such as urea peroxide or persalts such as perborates, percarbonates and persulfates, hydrogen peroxide and persulfates being particularly preferred.

The role of the chemical oxidizing agent is to degrade the melanin of the hair, which, depending on the nature of the oxidizing agent and the pH conditions, leads to more or less pronounced lightening of the fibres.

The lightening or bleaching compositions are present in anhydrous or aqueous form and in various different delivery forms: for example in the form of powders, creams, gels, foams or pastes, containing alkaline compounds such as alkaline amines or silicates, and a peroxygenated reagent such as ammonium or alkali metal persulfates, perborates or percarbonates, that are diluted at the time of use with an aqueous hydrogen peroxide composition.

The lightening or bleaching compositions may also result from mixing, at the time of use, an anhydrous powder containing the peroxygenated reagent with an aqueous composition containing the alkaline compounds and another aqueous composition containing hydrogen peroxide.

Moreover, the keratin materials may also be bleached by means of a standard process involving applying to said materials an aqueous composition comprising at least one oxidizing agent.

Thus, for relatively mild lightening, the oxidizing agent is generally hydrogen peroxide. When greater lightening is desired, peroxygenated salts, for instance persulfates, are usually used in the presence of hydrogen peroxide.

To make a lightening or bleaching product for keratin materials that is more effective in terms of lightening and/or speed, it is currently necessary to combine hydrogen peroxide with an alkaline agent or persulfate salts with a basic pH to obtain adequate formation of active oxygen.

However, such a combination commonly causes degradation of the keratin materials, in particular keratin fibres, and may possibly lead to varying degrees of skin irritation.

Thus, there is a real need to use compounds which do not have the drawbacks mentioned above, i.e. which can produce, under safer conditions than for persulfates, powerful lightening of keratin materials, in particular of keratin fibres, while at the same time minimizing their degradation.

The Applicant has thus discovered, surprisingly, that the use of one or more dihydroisoquinolinium salts of formula (I), as defined below, makes it possible especially to improve the oxidizing power of hydrogen peroxide, which allows greater lightening of keratin materials, in particular of keratin fibres, while at the same time minimizing their degradation.

In other words, the use of the compounds of formula (I) according to the invention improves the activity of hydrogen peroxide without the need to increase its concentration or the need to use persulfate salts at high concentrations, which minimizes the problems of sensitization of keratin materials.

Thus, the use of the dihydroisoquinolinium salt(s) according to the invention leads to greater lightening of keratin materials without, however, needing to increase the strength of the oxidizing agent.

In other words, the use of the dihydroisoquinolinium salt(s) according to the invention makes it possible to boost the oxidizing activity of chemical oxidizing agents, especially of hydrogen peroxide, leading to an improvement in the lightening of keratin materials relative to the use of the chemical oxidizing agent alone.

Furthermore, the dihydroisoquinolinium salts of formula (I) in combination with a chemical oxidizing agent, especially hydrogen peroxide, lead to more powerful lightening of the keratin materials than a chemical oxidizing agent alone.

A subject of the present invention is thus especially the use for treating keratin materials such as skin, preferably keratin fibres, especially human keratin fibres such as the hair, of one or more compounds of formula (I), and also the addition salts thereof and the solvates thereof:

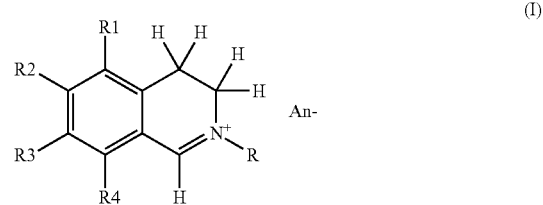

(I)

in which formula (I):
R represents a linear or branched $C_1$-$C_{20}$ alkyl radical, substituted with a group chosen from:
an amino group —$NR_5R_6$,
an amino group —$NR_7R_8$,
a carboxyl group —COOH,
a cyano group,
a halogen atom, an aminocarbonyl group —CONH$_2$,
a (C$_1$-C$_6$)alkoxycarbonyl group,
a saturated or unsaturated, optionally aromatic, 5- or 6-membered heterocycle, optionally substituted with one or more radicals, which may be identical or different, chosen from:
   a linear or branched C$_1$-C$_6$ alkyl radical,
   a linear or branched C$_1$-C$_6$ hydroxyalkyl radical,
   a C$_1$-C$_6$ alkoxy radical,
   a hydroxyl radical,
   an amino radical —NR$_5$R$_6$,
   a pyrrolidine, piperidine or morpholine radical,
   an ammonium radical N$^+$R$_a$R$_b$R$_c$ in which R$_a$, R$_b$ and R$_c$ denote, independently of each other, a linear or branched C$_1$-C$_6$ alkyl radical or a C$_1$-C$_6$ hydroxyalkyl radical,
a saturated or unsaturated, optionally aromatic, 5- or 6-membered cationic heterocycle optionally substituted with one or more radicals, which may be identical or different, chosen from a linear or branched C$_1$-C$_6$ alkyl radical, a C$_1$-C$_6$ hydroxyalkyl radical, a C$_1$-C$_6$ alkoxy radical, a hydroxyl radical and an amino radical —NR$_5$R$_6$;
an ammonium radical N$^+$R$_a$R$_b$R$_c$ in which R$_a$, R$_b$ and R$_c$ denote, independently of each other, a linear or branched C$_1$-C$_6$ alkyl radical or a C$_1$-C$_6$ hydroxyalkyl radical,
it being understood that when R represents an alkyl radical substituted with a cationic group, then the electrical neutrality of the compounds of formula (I) is ensured by the presence of one or more cosmetically acceptable anions X$^-$, X$^-$ adding to the anion An$^-$,
R$_1$, R$_2$, R$_3$ and R$_4$ represent, independently of each other, a radical chosen from:
a hydrogen atom,
a linear or branched C$_1$-C$_6$ alkyl radical optionally substituted with one or more groups, which may be identical or different, chosen from hydroxyl, C$_1$-C$_6$ alkoxy and amino —NR$_5$R$_6$ groups,
a hydroxyl radical,
an amino radical —NR$_5$R$_6$,
a C$_1$-C$_6$ alkoxy radical,
an aminocarbonyl radical —CONH$_2$,
a carboxyl radical —COOH,
R$_5$ and R$_6$, which may be identical or different, denote a hydrogen atom or a linear or branched C$_1$-C$_6$ alkyl radical,
R$_7$ and R$_8$, which may be identical or different, denote a linear or branched C$_1$-C$_6$ alkyl radical, substituted with a hydroxyl group,
An$^-$ and X$^-$ represent a cosmetically acceptable anion or mixture of anions intended to ensure the electrical neutrality of the compounds of formula (I); more particularly, An$^-$ is chosen from i) a halide such as a chloride or a bromide; ii) a nitrate; iii) a sulfonate including C$_1$-C$_6$ alkylsulfonates: Alk-S(O)$_2$O$^-$ such as methanesulfonate or mesylate and ethanesulfonate; iv) an arylsulfonate: Ar—S(O)$_2$O$^-$ such as benzenesulfonate and toluenesulfonate or tosylate; v) citrate; vi) succinate; vii) tartrate; viii) lactate; ix) an alkyl sulfate: Alk-O—S(O)O$^-$ such as methyl sulfate and ethyl sulfate; x) an aryl sulfate: Ar—O—S(O)O$^-$ such as benzene sulfate and toluene sulfate; xi) an alkoxy sulfate: Alk-O—S(O)$_2$O$^-$ such as methoxy sulfate and ethoxy sulfate; xii) an aryloxy sulfate: Ar—O—S(O)$_2$O$^-$, xiii) a phosphate O=P(OH)$_2$—O$^-$, O=P(O$^-$)$_2$—OH, O=P(O$^-$)$_3$, HO—[P(O)(O$^-$)]$_w$—P(O)(O$^-$)$_2$ with w being an integer between 1 and 15; xiv) acetate; xv) triflate; and xvi) a borate such as tetrafluoroborate, xvii) a disulfate (O=)$_2$S(O$^-$)$_2$ or SO$_4^{2-}$; xviii) monosulfate HSO$_4^-$.

The compound(s) of formula (I) thus defined thus correspond to substituted dihydroisoquinolinium salts and act as oxidation activators.

In particular, the compound(s) of formula (I) thus defined correspond to dihydroisoquinolinium salts in which the radical R is a substituted alkyl radical.

The compound(s) of formula (I) according to the invention may be used in the presence of one or more chemical oxidizing agents for lightening keratin materials, preferably keratin fibres, in particular human keratin fibres such as the hair.

The compound(s) of formula (I) are used in a non-therapeutic way.

The present invention also relates a process for treating keratin materials, preferably keratin fibres, especially human keratin fibres such as the hair, which consists in applying to said materials one or more compounds of formula (I), and also the addition salts thereof and the solvates thereof.

The process is non-therapeutic.

Preferably, the process according to the invention consists in applying to keratin materials said compound(s) of formula (I) and one or more chemical oxidizing agents.

Moreover, a subject of the invention is a composition for lightening keratin materials such as skin, preferably keratin fibres, especially human keratin fibres such as the hair, comprising one or more compounds of formula (I), and also the addition salts thereof and the solvates thereof, and one or more chemical oxidizing agents.

Similarly, the invention relates to the use of said composition for lightening keratin materials, preferably keratin fibres and skin, especially human keratin fibres such as the hair.

In addition, the present invention relates to one or more particular compounds of formula (II'), and also the addition salts thereof and the solvates thereof such as the hydrates:

$$\text{(II')}$$

in which formula (II'):
R' represents a linear or branched C$_1$-C$_{20}$ alkyl radical, substituted with a group chosen from:
a group —NR'$_5$R'$_6$,
a group —NR$_7$R$_8$,
a cyano group,
a halogen atom,
an aminocarbonyl group —CONH$_2$,
a (C$_2$-C$_6$)alkoxycarbonyl group,
a saturated or unsaturated, optionally aromatic, 5- or 6-membered cationic heterocycle, optionally substituted with one or more radicals, which may be identical or different, chosen from:
   a linear or branched C$_1$-C$_6$ alkyl radical,
   a C$_1$-C$_6$ hydroxyalkyl radical,
   a C$_1$-C$_6$ alkoxy radical, a hydroxyl radical,
an amino radical —NR$_5$R$_6$,
an ammonium radical N$^+$R$_a$R$_b$R$_c$ in which R$_a$, R$_b$ and R$_c$ denote, independently of each other, a linear or branched C$_1$-C$_6$ alkyl radical or a C$_1$-C$_6$ hydroxyalkyl radical,
a saturated or unsaturated, optionally aromatic, 5- or 6-membered heterocycle, chosen from:

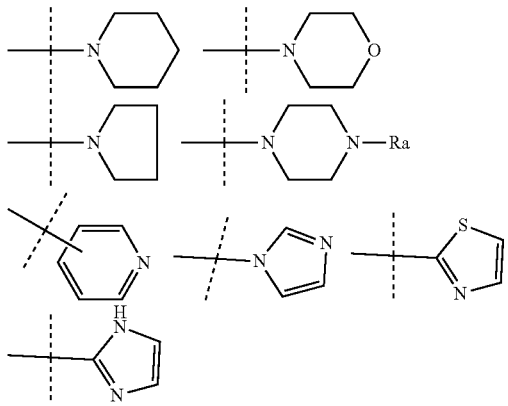

said heterocycle being optionally substituted with one or more radicals, which may be identical or different, chosen from:
  a linear or branched C$_1$-C$_6$ alkyl radical,
  a linear or branched C$_1$-C$_6$ hydroxyalkyl radical,
  a C$_1$-C$_6$ alkoxy radical,
  a hydroxyl radical,
  an amino radical —NR$_5$R$_6$,
  a pyrrolidine, piperidine or morpholine radical,
  an ammonium radical N$^+$R$_a$R$_b$R$_c$ in which R$_a$, R$_b$ and R$_c$ denote, independently of each other, a linear or branched C$_1$-C$_6$ alkyl radical or a C$_1$-C$_6$ hydroxyalkyl radical;
it being understood that when R' represents an alkyl radical substituted with a cationic group, then the electrical neutrality of the compounds of formula (II') is ensured by the presence of one or more cosmetically acceptable anions X$^-$, X$^-$ adding to the anion An$^-$,
R'$_1$, R'$_2$, R'$_3$ and R'$_4$ represent, independently of each other, a radical chosen from:
a hydrogen atom,
a linear or branched C$_1$-C$_6$ alkyl radical optionally substituted with one or more groups, which may be identical or different, chosen from hydroxyl, C$_1$-C$_6$ alkoxy and amino —NR$_5$R$_6$ groups,
an amino radical —NR$_5$R$_6$,
an amino radical —NH$_2$,
an aminocarbonyl radical —CONH$_2$,
a carboxyl radical —COOH,
R'$_5$ and R'$_6$, which may be identical or different, denote a hydrogen atom or a linear or branched C$_1$-C$_6$ alkyl radical, it being noted that R'$_5$ and R'$_6$ cannot simultaneously be a hydrogen atom,
R$_7$ and R$_8$, which may be identical or different, denote a linear or branched C$_1$-C$_6$ alkyl radical, substituted with a hydroxyl group,
R$_5$ and R$_6$, which may be identical or different, denote a hydrogen atom or a linear or branched C$_1$-C$_6$ alkyl radical, An'$^-$ and X'$^-$ representing a cosmetically acceptable anion or mixture of anions intended to ensure the electrical neutrality of the compounds of formula (II); more particularly, An'$^-$ and X$^-$ are chosen from:
a chloride, a bromide
a sulfonate including C$_1$-C$_6$ alkylsulfonates: Alk-S(O)$_2$O$^-$ such as methanesulfonate or mesylate and ethane-sulfonate
an arylsulfonate: Ar—S(O)$_2$O$^-$ such as benzenesulfonate and toluenesulfonate or tosylate;
citrate
succinate
tartrate
lactate
an alkyl sulfate: Alk-O—S(O)O$^-$ such as methyl sulfate and ethyl sulfate
an aryl sulfate: Ar—O—S(O)O$^-$ such as benzene sulfate and toluene sulfate
an alkoxy sulfate: Alk-O—S(O)$_2$O$^-$ such as methoxy sulfate and ethoxy sulfate
an aryloxy sulfate: Ar—O—S(O)$_2$O$^-$
a phosphate O=P(OH)$_2$—O—, O=P(O$^-$)$_2$—OH, O=P(O$^-$)$_3$, HO—[P(O)(O$^-$)]$_w$—P(O)(O$^-$)$_2$ with w being an integer between 1 and 15
acetate
disulfate (O=)$_2$S(O$^-$)$_2$ or SO$_4^2$ and monosulfate HSO$_4^-$
carbonate CO$_3^{2-}$ and hydrogen carbonate HCO$_3^-$
it being understood that compound (II') is different from the compound:

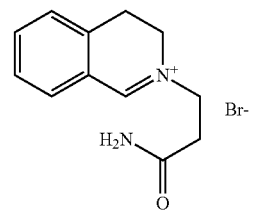 [SMILES: NC(=O)CC[N+]1=Cc2ccccc2CC1 ; [Br-]]

Preferably, compound (II') is also different from the compound:

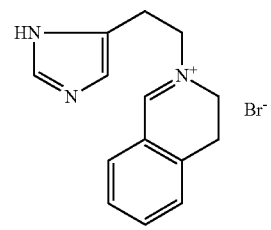 [SMILES: C1=[N+](CCc2cnc[nH]2)CCc2ccccc21 ; [Br-]]

Preferably, when R' represents a linear or branched C$_1$-C$_{20}$ alkyl radical, substituted with a saturated or unsaturated, optionally aromatic, 5- or 6-membered heterocycle, the latter is chosen from:

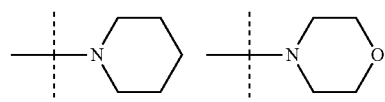

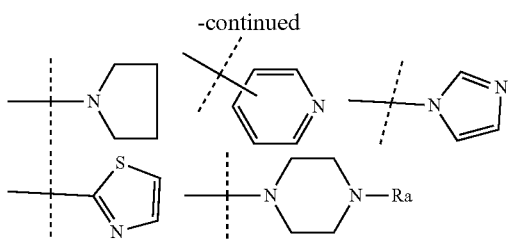

Preferably, R'$_1$, R'$_2$, R'$_3$ and R'$_4$ represent a hydrogen atom.

Similarly, another subject of the present invention relates to a composition comprising said compound(s) of formula (II'), and also the addition salts thereof and the solvates thereof.

Other subjects, characteristics, aspects and advantages of the invention will emerge even more clearly on reading the description and the examples that follow.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more". In addition, the expression "at least two" is equivalent to the expression "two or more".

The term "addition salts of the compounds of formulae (I) and (II') according to the invention" thus means addition salts with an organic or mineral acid, and addition salts with an organic or mineral base.

The addition salts of the compounds of formulae (I) and (II') according to the invention are in particular chosen from addition salts with an acid, such as hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, ammonia, amines or alkanolamines.

Moreover, the solvates of the compounds of formulae (I) and (II') according to the invention more particularly represent the hydrates of said compounds and/or the combination of said compounds with a linear or branched $C_1$ to $C_4$ alcohol such as methanol, ethanol, isopropanol or n-propanol. Preferably, the solvates are hydrates.

Use of the Compounds of Formula (I)

An$^-$ and X$^-$ represent, independently of each other, an organic or mineral anion or mixture of anions which ensures the electrical neutrality of the compounds of formula (I).

Preferably, An$^-$ and X$^-$ represent, independently of each other, an anion chosen from halides, in particular chloride and bromide; ($C_1$-$C_6$)alkylsulfonates chosen from methanesulfonate or mesylate and ethanesulfonate; arylsulfonates chosen from benzenesulfonate and toluenesulfonate or tosylate; tartrate; citrate; lactate; succinate; ($C_1$-$C_6$)alkyl sulfates chosen from methyl sulfate and ethyl sulfate; aryl sulfates chosen from benzene sulfate and toluene sulfate; alkoxy sulfates chosen from methoxy sulfate and ethoxy sulfate; the phosphates as defined previously; acetate, disulfate and carbonate.

Preferably, An$^-$ is an anion chosen from halides, in particular chloride and bromide.

Preferably, X$^-$ corresponds to para-toluenesulfonate.

According to one embodiment, An$^-$ is an anion chosen from halides, in particular chloride and bromide, and X$^-$ corresponds to para-toluenesulfonate.

According to a preferred embodiment, R represents a linear $C_1$-$C_6$ and preferably linear $C_1$-$C_4$ alkyl radical, substituted with the groups mentioned previously.

According to one embodiment, at least one of the radicals $R_1$, $R_2$, $R_3$ or $R_4$ represents a hydrogen atom.

According to a preferred embodiment, $R_1$, $R_2$, $R_3$ and $R_4$ are identical.

In accordance with this embodiment, $R_1$, $R_2$, $R_3$ and $R_4$ are identical and preferably represent a hydrogen atom.

According to a preferred embodiment, $R_1$, $R_2$, $R_3$ and $R_4$ represent a hydrogen atom and R represents a linear $C_1$-$C_4$ alkyl radical, substituted with the groups mentioned previously.

According to one embodiment, R represents a $C_1$-$C_{20}$ alkyl radical substituted with a cationic group.

The cationic group may be an ammonium radical N$^+$R$_a$R$_b$R$_c$ as defined previously or a heterocycle bearing an endocyclic or exocyclic cationic charge.

In accordance with this embodiment, R represents a $C_1$-$C_{20}$ alkyl radical substituted with:
  a saturated or unsaturated, optionally aromatic, 5- or 6-membered heterocycle, substituted with an ammonium radical N$^+$R$_a$R$_b$R$_c$ in which R$_a$, R$_b$ and R$_c$ denote, independently of each other, a linear or branched $C_1$-$C_6$ alkyl radical or a $C_1$-$C_6$ hydroxyalkyl radical,
  a saturated or unsaturated, optionally aromatic, 5- or 6-membered cationic heterocycle optionally substituted with one or more radicals, which may be identical or different, chosen from a linear or branched $C_1$-$C_6$ alkyl radical, a $C_1$-$C_6$ hydroxyalkyl radical, a $C_1$-$C_6$ alkoxy radical, a hydroxyl radical and an amino radical —NR$_5$R$_6$;
  an ammonium radical N$^+$R$_a$R$_b$R$_c$ in which R$_a$, R$_b$ and R$_c$ denote, independently of each other, a linear or branched $C_1$-$C_6$ alkyl radical or a $C_1$-$C_6$ hydroxyalkyl radical, it being understood that the electrical neutrality of the compounds of formula (I) is ensured by the presence of one or more cosmetically acceptable anions X$^-$, X$^-$ preferably being para-toluenesulfonate.

In accordance with this embodiment, R represents a linear $C_1$-$C_6$ and preferably linear $C_1$-$C_4$ alkyl radical.

Even more preferentially, in accordance with this embodiment, $R_1$, $R_2$, $R_3$ and $R_4$ represent a hydrogen atom.

Even more preferentially, in accordance with this embodiment, the ammonium radical corresponds to a radical in which R$_a$, R$_b$ and R$_c$ denote, independently of each other, a $C_1$-$C_3$ and in particular $C_1$ alkyl radical.

According to another embodiment, R represents a $C_1$-$C_{20}$ alkyl radical substituted with a non-cationic group.

In accordance with this embodiment, R represents a $C_1$-$C_{20}$ alkyl radical substituted with:
  an amino group —NR$_5$R$_6$,
  an amino group —NR$_7$R$_8$,
  a carboxyl group —COOH,
  a cyano group,
  a halogen atom,
  an aminocarbonyl group —CONH$_2$,
  a ($C_1$-$C_6$)alkoxycarbonyl group,
  a saturated or unsaturated, optionally aromatic, 5- or 6-membered heterocycle, optionally substituted with one or more radicals, which may be identical or different, chosen from:
    a linear or branched $C_1$-$C_6$ alkyl radical,
    a linear or branched $C_1$-$C_6$ hydroxyalkyl radical,
    a $C_1$-$C_6$ alkoxy radical,
    a hydroxyl radical, an amino radical —NR$_5$R$_6$,
a pyrrolidine, piperidine or morpholine radical.

In accordance with this embodiment, R represents a linear C$_1$-C$_6$ and preferably C$_1$-C$_4$ alkyl radical.

Even more preferentially, in accordance with this embodiment, R$_1$, R$_2$, R$_3$ and R$_4$ represent a hydrogen atom.

Preferably, the compound(s) of formula (I) as defined above are chosen from the compound(s) of formula (II), and also the addition salts thereof and the solvates thereof:

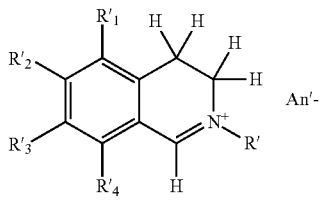

(II)

in which formula (II) R', R'$_1$, R'$_2$, R'$_3$, R'$_4$ and An'$^-$ have the definitions mentioned previously.

Preferably, An'$^-$ is an anion chosen from halides, in particular chloride and bromide.

Preferably, X'$^-$ corresponds to para-toluenesulfonate.

According to a preferred embodiment, R'$_1$, R'$_2$, R'$_3$ and R'$_4$ are identical.

In accordance with this embodiment, R'$_1$, R'$_2$, R'$_3$ and R'$_4$ are identical and preferably represent a hydrogen atom.

Preferably, R' represents a linear C$_1$-C$_6$ and preferably C$_1$-C$_4$ alkyl radical, substituted with the groups mentioned previously.

According to a preferred embodiment, R'$_1$, R'$_2$, R'$_3$ and R'$_4$ represent a hydrogen atom and R' represents a linear C$_1$-C$_4$ alkyl radical, substituted with the groups mentioned previously.

According to one embodiment, R' represents a linear C$_1$-C$_6$ alkyl radical substituted with:
a group —NR'$_5$R'$_6$,
a cyano group,
a halogen atom,
a (C$_2$-C$_6$)alkoxycarbonyl group,
a saturated or unsaturated, optionally aromatic, 5- or 6-membered cationic heterocycle chosen from the following formulae:

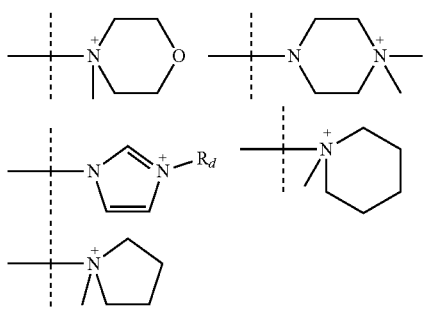

Rd corresponding to a linear C$_1$-C$_4$ and preferably C$_1$ alkyl radical,
an ammonium radical N$^+$R$_a$R$_b$R$_c$ in which R$_a$, R$_b$ and R$_c$ denote, independently of each other, a C$_1$-C$_3$ and preferably C$_1$ alkyl radical, a saturated or unsaturated, optionally aromatic, 5- or 6-membered heterocycle, chosen from:

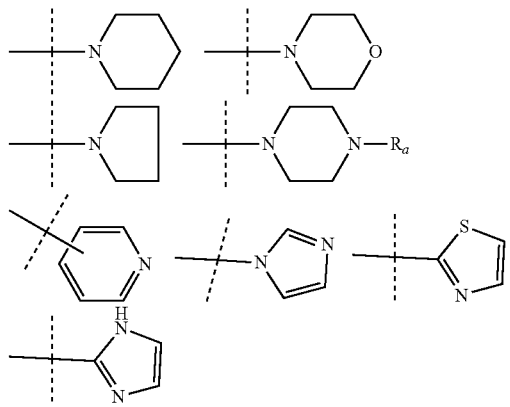

in which Ra corresponds to a C$_1$-C$_3$ and preferably C$_1$ alkyl radical,
said heterocycle being optionally substituted with an amino radical —NR$_5$R$_6$ in which R$_5$ and R$_6$ represent a C$_1$-C$_3$ alkyl radical or an ammonium radical N$^+$R$_a$R$_b$R$_c$ in which R$_a$, R$_b$ and R$_c$ denote, independently of each other, a C$_1$-C$_3$ alkyl radical.

According to one embodiment, the cationic heterocycle is chosen from:

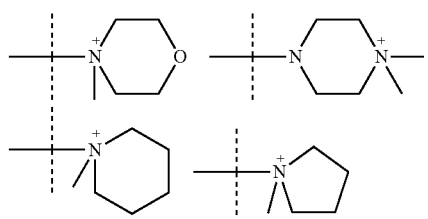

According to another embodiment, the cationic heterocycle is aromatic and especially corresponds to:

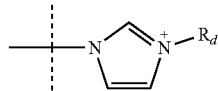

in which Rd corresponds to a linear C$_1$-C$_4$ and preferably C$_1$ alkyl radical.

According to one embodiment, the heterocycle is chosen from:

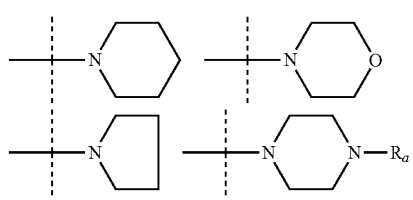

According to one embodiment, the heterocycle is aromatic and is chosen from:

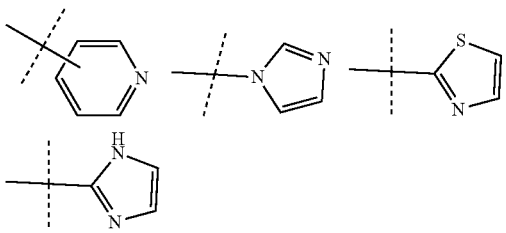

The compound(s) of formula (I) are preferentially chosen from the following compounds, the addition salts thereof and also the solvates thereof:

Compound 1

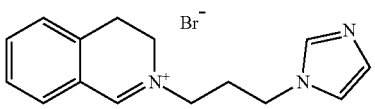

2-(3-imidazol-1-ylpropyl)-3,4-dihydroisoquinolinium bromide

Compound 2

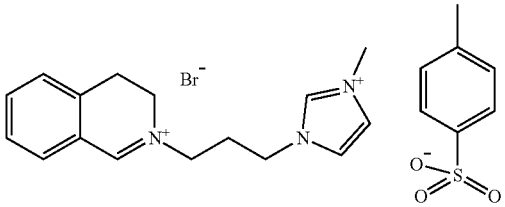

2-[3-(3-methyl-1H-imidazol-3-ium-1-yl)propyl]-3,4-dihydroisoquinolinium bromide 4-methylbenzenesulfonate Compound 3

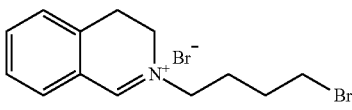

2-(4-bromobutyl)-3,4-dihydroisoquinolinium bromide

Compound 4

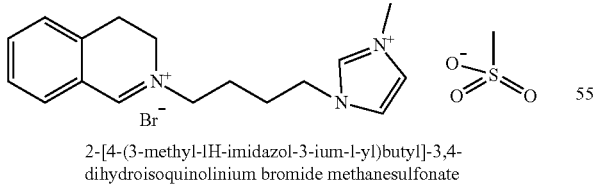

2-[4-(3-methyl-1H-imidazol-3-ium-1-yl)butyl]-3,4-dihydroisoquinolinium bromide methanesulfonate Compound 5

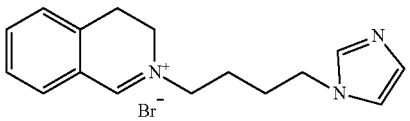

2-(4-imidazol-1-ylbutyl)-3,4-dihydroisoquinolinium bromide

Compound 6

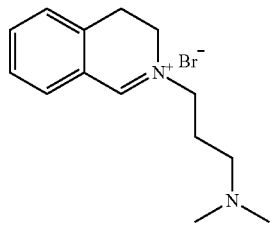

2-(3-dimethylaminopropyl)-3,4-dihydroisoquinolinium bromide

Compound 7

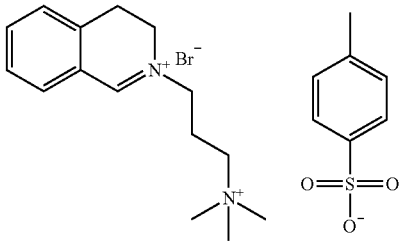

2-[3-(trimethylammonio)propyl]-3,4-dihydroisoquinolinium bromide 4-methylbenzenesulfonate Compound 8

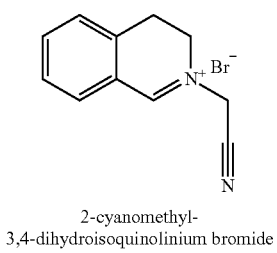

2-cyanomethyl-3,4-dihydroisoquinolinium bromide

Compound 9

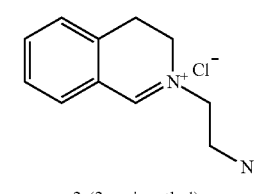

2-(2-aminoethyl)-3,4-dihydroisoquinolinium chloride

Compound 10

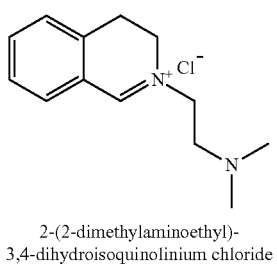

2-(2-dimethylaminoethyl)-3,4-dihydroisoquinolinium chloride

-continued

Compound 11

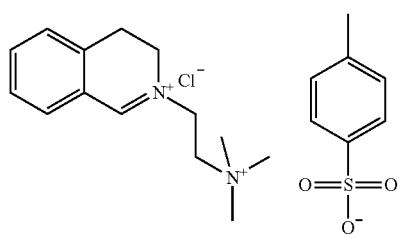

2-[2-(trimethylammonio)ethyl]-
3,4-dihydroisoquinolinium chloride
4-methylbenzenesulfonate Compound 12

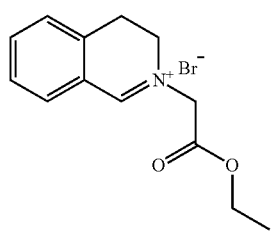

2-ethoxycarbonylmethyl-3,4-
dihydroisoquinolinium bromide

Compound 13

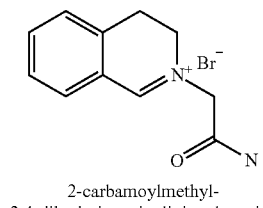

2-carbamoylmethyl-
3,4-dihydroisoquinolinium bromide

Compound 14

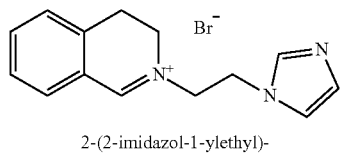

2-(2-imidazol-1-ylethyl)-
3,4-dihydroisoquinolinium bromide

Compound 15

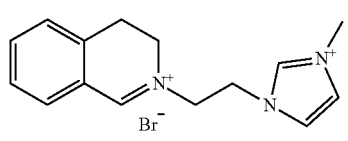

2-[3-(3-methyl-]1H-imidazol-3-ium-1-yl)ethyl]-
3,4-dihydroisoquinolinium bromide
4-methylbenzenesulfonate Compound 16

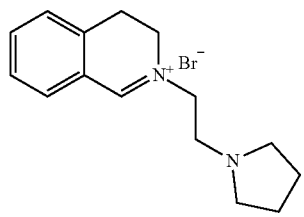

2-(2-pyrrolidin-1-ylethyl)-
3,4-dihydroisoquinolinium bromide

Compound 17

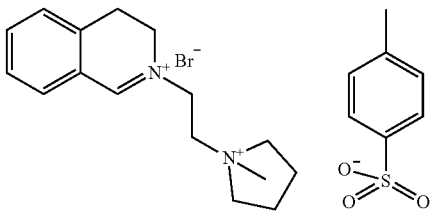

2-[2-(1-methylpyrrolidinium-1-yl)ethyl]
-3,4-dihydroisoquinolinium bromide
4-methylbenzenesulfonate Compound 18

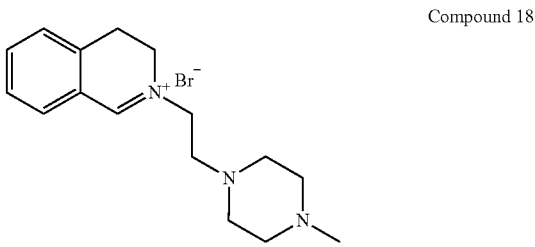

[2-(4-methylpiperazin-1-yl)ethyl]
-3,4-dihydroisoquinolinium bromide

Compound 19

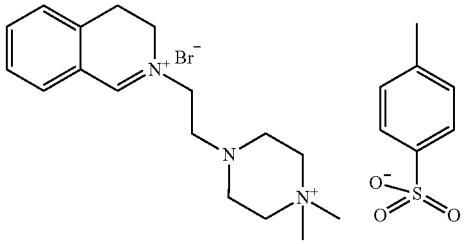

2-[2-(4,4-dimethylpiperazin-4-ium-1-yl)ethyl]
-3,4-dihydroisoquinolinium bromide
4-methylbenzenesulfonate Compound 20

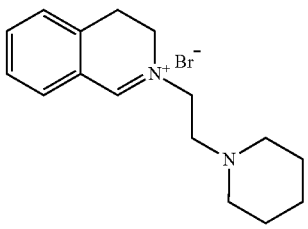

2-(2-piperidin-1-ylethyl)-
3,4-dihydroisoquinolinium bromide

Compound 21

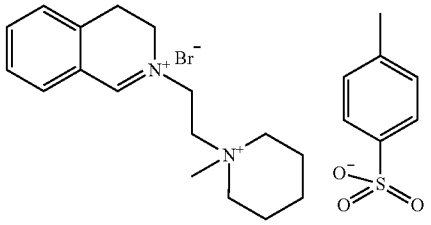

2-[2-(1-methylpiperidinium-1-yl)ethyl]-
3,4- dihydroisoquinolinium bromide
4-methylbenzenesulfonate -continued Compound 22

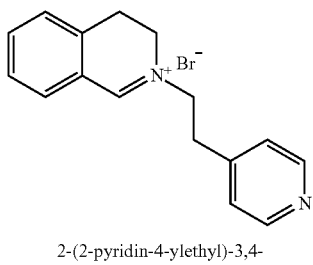

2-(2-pyridin-4-ylethyl)-3,4-
dihydroisoquinolinium bromide

Compound 23

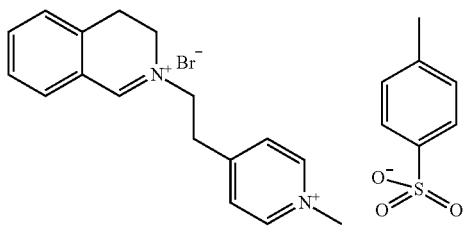

2-[2-(1-methylpyridinium-4-yl)ethyl]-
3,4-dihydroisoquinolinium bromide
4-methylbenzenesulfonate Compound 24

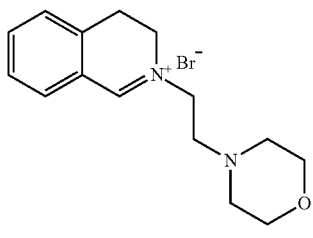

2-(2-morpholin-4-ylethyl)-
3,4-dihydroisoquinolinium bromide

Compound 25

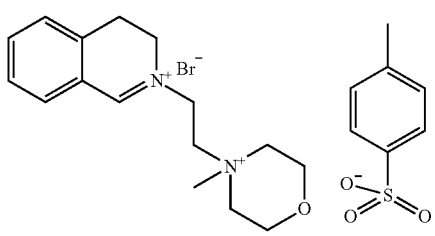

2-[2-(4-methylmorpholin-4-ium-4-yl)ethyl]-
3,4-dihydroisoquinolinium bromide
4-methylbenzenesulfonate Compound 26

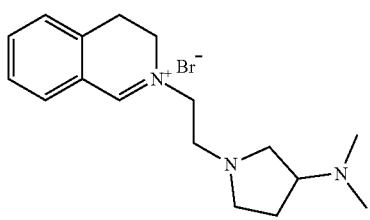

2-[2-(3-dimethylaminopyrrolidin-1-yl)ethyl]-
3,4-dihydroisoquinolinium bromide

Compound 27

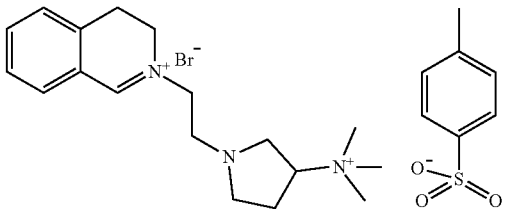

2-{2-[3-(trimethylammonio)pyrrolidin-1-yl]ethyl}-
3,4-dihydroisoquinolinium bromid
4-methylbenzenesulfonate As indicated previously, the compound(s) of formula (I) according to the invention, preferably compounds 1 to 27, the addition salts thereof and the solvates thereof may be used in the presence of one or more chemical oxidizing agents for lightening keratin materials such as skin, preferably keratin fibres, in particular human keratin fibres such as the hair.

The chemical oxidizing agents are such as those described herein below.

Composition Containing Compounds of Formula (I)

Thus, the invention relates to a composition comprising the compound(s) of formula (I), preferably the compound(s) of formula (II), as defined above, and also the addition salts thereof and the solvates thereof, and one or more chemical oxidizing agents.

Preferably, the composition according to the invention comprises one or more compounds of formula (I) chosen from compounds 1 to 27.

The composition according to the invention lightens keratin materials, especially keratin fibres and preferably human keratin fibres such as the hair, using less chemical oxidizing agent.

For the purposes of the present invention, the term "chemical oxidizing agent" means an oxidizing agent other than atmospheric oxygen.

The oxidizing agent(s) used in the invention are for example hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases.

More particularly, the chemical oxidizing agent(s) are chosen from hydrogen peroxide, urea peroxide, alkali metal bromates, peroxygenated salts, for instance persulfates, perborates, peracids and precursors thereof and percarbonates of alkali metals or alkaline-earth metals.

The compound(s) of formula (I) and the addition salts thereof and the solvates thereof may be present in the composition according to the invention in a content ranging from 0.01% to 10% by weight, preferably in a content ranging from 0.5% to 3% by weight, more preferably ranging from 1% to 3% by weight relative to the total weight of the composition.

Preferentially, the chemical oxidizing agent is hydrogen peroxide.

According to one embodiment, the composition according to the invention comprises one or more compounds of formula (I), preferably of formula (II), and the addition salts thereof and the solvates thereof, and at least one chemical oxidizing agent such as hydrogen peroxide.

In accordance with this embodiment, the composition preferably additionally comprises one or more persulfates.

In other words, the composition may preferentially comprise a mixture of hydrogen peroxide and persulfates.

According to one embodiment, the composition according to the invention comprises one or more compounds of formula (I), preferably of formula (II), and the addition salts thereof and the solvates thereof, and hydrogen peroxide as chemical oxidizing agent; said composition being free of persulfates.

Preferably, the composition according to the invention may comprise one or more alkaline agents, especially organic or mineral alkaline agents.

The mineral alkaline agent(s) are preferably chosen from aqueous ammonia, ammonium halides, in particular ammonium chloride, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a $pK_b$ at 25° C. of less than 12, preferably less than 10. It should be noted that it is the $pK_b$ corresponding to the function of highest basicity. In addition, the organic amines do not comprise any alkyl or alkenyl fatty chain comprising more than ten carbon atoms.

The organic alkaline agent(s) are chosen, for example, from alkanolamines, oxyethylenated and/or oxypropylenated ethylenediamines, amino acids and the compounds of formula (III) below:

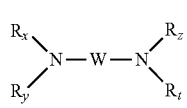

in which formula (III) W is a divalent $C_1$-$C_6$ alkylene radical optionally substituted with one or more hydroxyl groups or a $C_1$-$C_6$ alkyl radical, and/or optionally interrupted with one or more heteroatoms such as O, or —$NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

The term "alkanolamine" means an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$-$C_1$ hydroxyalkyl radicals are in particular suitable for performing the invention.

Among the compounds of this type, mention may be made of monoethanolamine (MEA), diethanolamine, triethanolamine, mono isopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine and salts thereof.

Advantageously, the amino acids are basic amino acids comprising an additional amine function optionally included in a ring or in a ureido function.

Such basic amino acids are preferably chosen from those corresponding to formula (IV) below, and also salts thereof:

in which R represents a group chosen from imidazolyl, preferably imidazolyl-4-yl; aminopropyl; amino ethyl; —$(CH_2)_2NH$—$C(O)$—$NH_2$; and —$(CH_2)_2$—$NH$—$C(NH)$—$NH_2$.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidino alanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) present in the composition according to the invention are chosen from aqueous ammonia, alkanolamines, amino acids in neutral or ionic form, in particular basic amino acids, and preferably corresponding to those of formula (IV).

More preferentially, the alkaline agent(s) present in the composition according to the invention are chosen from aqueous ammonia and alkanolamines, and mixtures thereof.

More preferentially, the alkaline agent(s) present in the composition according to the invention are chosen from aqueous ammonia and ammonium chloride.

According to a particular embodiment of the invention, the alkaline agent(s) are mineral.

According to one particular embodiment of the invention, the alkaline agent(s) are organic such as alkanolamines, particularly monoethanolamine.

The quantity of alkaline agent(s) present in the composition according to the invention may range from 0.01% to 30% by weight, and preferably from 0.1% to 20% by weight relative to the total weight of the composition.

The composition according to the invention has a pH greater than or equal to 4. Preferably, the pH of the composition according to the invention varies from 7 to 11, more preferentially from 8 to 10 and more preferentially from 8.5 to 9.5.

According to one embodiment, the composition according to the invention comprises one or more compounds of formula (II) and the addition salts thereof and the solvates thereof, one or more chemical oxidizing agents and one or more alkaline agents chosen from aqueous ammonia and ammonium halides such as ammonium chloride.

In accordance with this embodiment, the compound of formula (II) is preferably chosen from compounds 1 to 8 and 10 to 27 as described above.

In accordance with this embodiment, the chemical oxidizing agent is preferably hydrogen peroxide.

The composition according to the invention may optionally comprise one or more additives, different from the compounds of the invention and among which mention may be made of organic solvents, cationic, anionic, nonionic or amphoteric polymers or mixtures thereof, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, especially polymeric thickeners, opacifiers or nacreous agents, antioxidants, hydroxy acids, fragrances, preserving agents, pigments and ceramides.

Needless to say, those skilled in the art will take care to select this or these optional additional compound(s) such that the advantageous properties intrinsically associated with the composition according to the invention are not, or are not substantially, adversely affected by the envisaged addition(s).

The above additives may generally be present in an amount, for each of them, of between 0 and 20% by weight relative to the total weight of the composition.

The composition according to the invention preferentially comprises a physiologically acceptable medium.

For the purposes of the present invention, the term "physiologically acceptable medium" is intended to mean a medium that is suitable for the topical administration of a composition. A physiologically acceptable medium is preferentially a cosmetically or dermatologically acceptable medium, i.e. a medium that has no unpleasant odour or appearance, and that is entirely compatible with the topical administration route. In the present case, where the composition is intended for topical administration, that is to say for administration by application at the surface of the keratin material under consideration, such a medium is considered in particular to be physiologically acceptable when it does not cause stinging, tightness or redness unacceptable to the user.

Treatment Process According to the Invention

The process for treating keratin materials consists in applying to said materials one or more compounds of formula (I) as defined above optionally in the presence of one or more chemical oxidizing agents.

The process deals with the treatment of keratin materials, especially human keratin materials such as skin and hair.

Preferably, the compound(s) of formula (I) according to the invention are applied in the presence of one or more chemical oxidizing agents, more preferentially hydrogen peroxide.

According to one embodiment, the treatment process consists in applying the composition as defined previously to keratin materials.

Preferably, the treatment process consists in applying the composition as defined previously on dry or wet keratin fibres. The composition is left in place on the fibres for a period, generally from 1 minute to 1 hour, preferably from 5 minutes to 30 minutes.

The temperature during the process is conventionally between room temperature (between 15 and 25° C.) and 80° C. and preferably between room temperature and 60° C.

Preferentially, the composition is applied at room temperature.

After the treatment, the keratin materials are optionally rinsed with water, optionally washed with a shampoo and then rinsed with water, before being dried or left to dry.

The composition according to the invention may be prepared by mixing at least two compositions.

The composition according to the invention may especially be obtained by mixing two compositions:
 a composition (A) comprising one or more compounds of formula (I) according to the invention, and
 a composition (B) comprising one or more chemical oxidizing agents.

Compounds of Formula (II') and Corresponding Composition

As indicated previously, the present invention also relates to compounds of formula (II') as defined previously, and also the addition salts thereof and the solvates thereof.

Preferably, the compounds of formula (II') are chosen from compounds 1-8 and 10-27.

The invention also relates to a composition comprising one or more compounds of formula (II') as defined previously.

Preferably, the composition comprises one or more compounds of formula (II') chosen from compounds 1-8 and 10-27 as described above.

The compound(s) of formula (II') and the addition salts thereof and the solvates thereof may be present in the composition according to the invention in a content ranging from 0.01 to 10% by weight, preferably in a content ranging from 0.5% to 3% by weight, more preferably ranging from 1% to 3% by weight relative to the total weight of the composition.

The composition preferentially comprises a physiologically acceptable medium.

Process for Preparing the Compounds of Formula (II')

The compounds of formula (II') may be obtained by quaternization of dihydroisoquinoline derivatives (1) with alkylating derivatives $R_1$-An (2) with An$^-$ representing a leaving group such as a halogen atom, in particular chlorine, bromine and iodine, an alkylsulfonate or an arylsulfonate.

Such a reaction generally takes place in the presence of a polar protic solvent, for example ethanol, and may be performed at room temperature (27° C.) and is accelerated by heating (at solvent reflux).

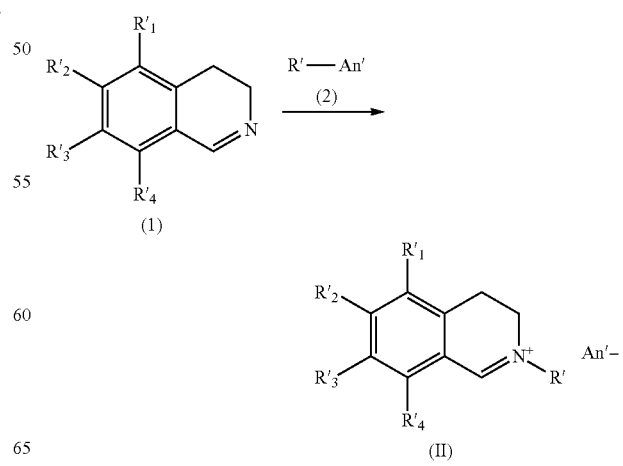

The compounds of formula (II') may also be obtained by simple counter-anion exchange with a salt $An'^-X^+$:

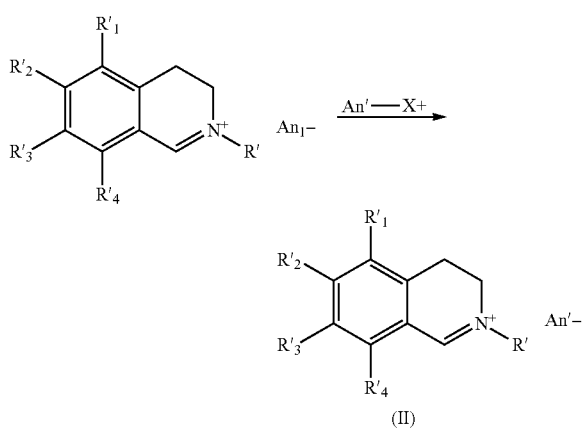

The compounds of formula (II') may also be obtained according to the synthetic approach below:

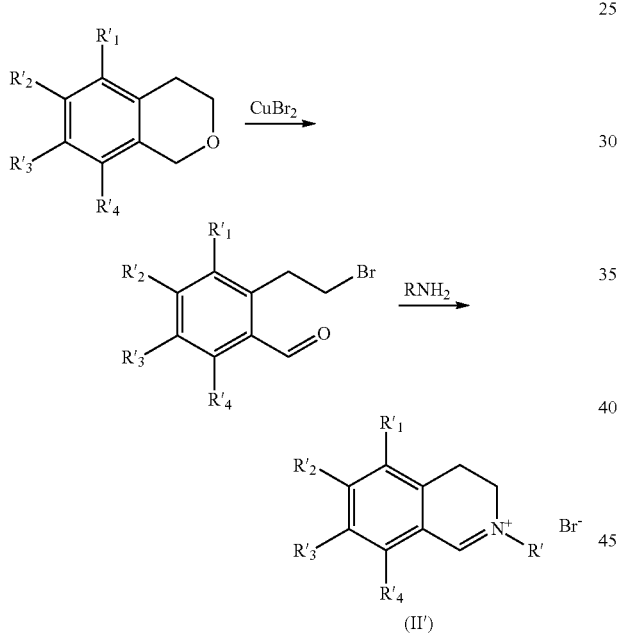

More precisely, the compounds of formulae (II) and (II') may be obtained by drawing on the bibliographic references below: Archiv der Pharmazie (Weinheim, Germany), 1988, vol. 321, pages 759-764, Journal of Organic Chemistry, 2014, vol. 10, pages 2981-2988, Tetrahedron, 2012, vol. 68, 26 pages 5137-5144, Heterocycles, 2004, vol. 63, 2 pages 401-409, Green Chemistry, 2014, vol. 16, 10 pages 4524-4529, Journal of Organic Chemistry, 1982, vol. 47, 12 pages 2308-2312, Tetrahedron, 1993, vol. 49, 2 pages 423-438, Synthesis, 1992, 9 pages 887-890, Journal of the American Chemical Society, 1949, vol. 71, pages 3405, 3407, Tetrahedron Letters, 1987, vol. 28, 48 pages 6061-6064.

The present invention also relates to the use of one or more compounds of formula (I) as defined previously, as oxidation activator.

In particular, the compound(s) of formula (I) according to the invention are used in the presence of one or more chemical oxidizing agents for improving the lightening of keratin materials, especially keratin fibres, preferably human keratin fibres such as the hair.

In other words, the compound(s) of formula (I) according to the invention are used for improving the oxidizing activity of one or more chemical oxidizing agents.

Preferably, the chemical oxidizing agent is hydrogen peroxide.

The examples that follow serve to illustrate the invention without, however, being limiting in nature.

In these examples, the colour of the locks was evaluated in the CIE L* a* b* system, using a Minolta Spectrophotometer CM2600D colorimeter.

In this L* a* b* system, the three parameters denote, respectively, the colour intensity (L*), the green/red colour axis (a*) and the blue/yellow colour axis (b*). The higher the value of L*, the lighter the colour. The higher the value of a*, the redder the colour and the higher the value of b*, the yellower the colour.

SYNTHETIC EXAMPLES

Example 1: Synthesis of 2-(3-imidazol-1-ylpropyl)-3,4-dihydroisoquinolinium bromide (Compound 1)

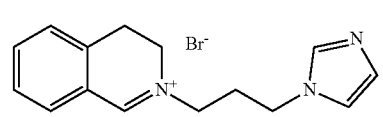

Step 1: Synthesis of 2-(2-bromoethyl)benzaldehyde (a)

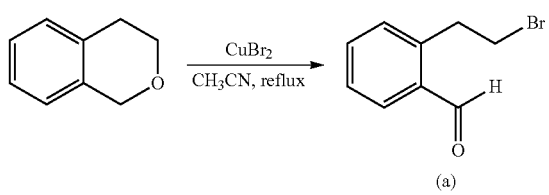

20 g of $CuBr_2$ (1.2 eq.) are added to 10 g of isochroman (1 eq.) dissolved in 200 mL of acetonitrile. The mixture is refluxed under nitrogen for 16 hours and then left at room temperature. The mixture is then poured onto ice and extracted three times with ethyl acetate. The organic phases are combined, washed with saturated aqueous NaCl solution and then dried over $Na_2SO_4$. The whole is filtered, evaporated to dryness and purified on a column of silica eluted with petroleum ether. 11.2 g (yield=70%) of compound (a) are obtained in the form of a yellow oil.

The NMR and mass analyses are in accordance with the expected structure.

Step 2: Synthesis of 2-(3-imidazol-1-ylpropyl)-3,4-dihydroisoquinolinium bromide (Compound 1)

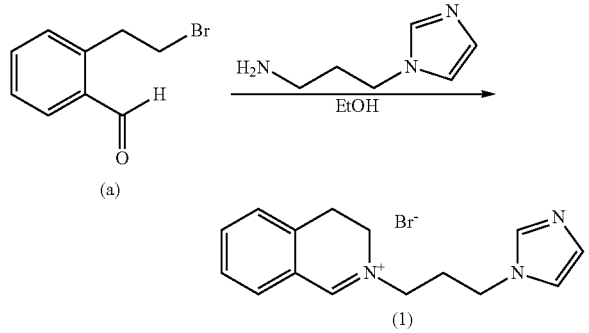

(a)

(1)

6.13 g (1.8 eq.) of 2-(2-bromoethyl)benzaldehyde are added without heating to a solution of 2 g of 3-imidazol-1-ylpropylamine in 20 mL of absolute ethanol. The mixture is stirred at room temperature for 16 hours and then poured into a large excess of petroleum ether. After stirring for 30 minutes, the oil formed is recovered after separation of the phases by settling, and washed three times with ethyl acetate. The oil is then purified on a column of silica. 2.5 g (yield=49%) of compound (1) are obtained in the form of an orange oil.

The NMR and mass analyses are in accordance with the expected structure.

Example 2: Synthesis of 2-[3-(3-methyl-1H-imidazol-3-ium-1-yl)propyl]-3,4-dihydroisoquinolinium bromide 4-methylbenzenesulfonate (Compound 2)

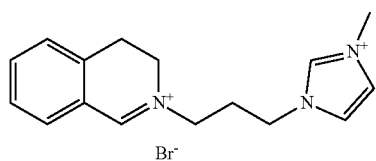

(2)

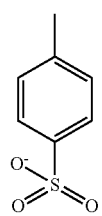

0.4 g (1.1 eq.) of methyl para-toluenesulfonate is added to 1 g of 2-(3-imidazol-1-ylpropyl)-3,4-dihydroisoquinolinium bromide dissolved in 50 mL of acetonitrile. The mixture is refluxed for 16 hours. After evaporating to dryness, the oil obtained is purified on a column of silica. 0.8 g (yield=51%) of compound 2 are obtained in the form of a brown oil.

The NMR and mass analyses are in accordance with the expected structure.

Example 3: Synthesis of 2-(4-bromobutyl)-3,4-dihydroisoquinolinium bromide (Compound 3)

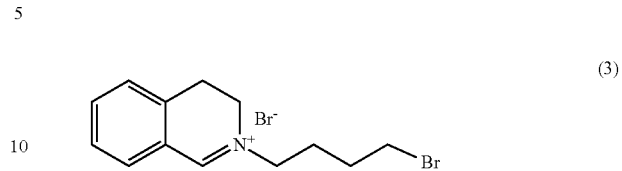

(3)

5 g (38.1 mmol; 1 eq.) of dihydroisoquinoline are added to 22.8 mL (190.6 mmol; 5 eq.) of 1,4-dibromobutane dissolved in 100 mL of toluene. The reaction medium is heated at 60° C. for 26 hours (monitoring by TLC, eluent: $CH_2Cl_2$/MeOH: 9/1). The reaction medium is left at room temperature and then filtered. The solid obtained is dried under vacuum in the presence of $P_2O_5$. 12.4 g (yield=94%) of compound 3 are obtained in the form of a beige-coloured solid.

The NMR and mass analyses are in accordance with the expected structure.

Example 4: Synthesis of 2-carbamoylmethyl-3,4-dihydroisoquinolinium bromide (Compound 13)

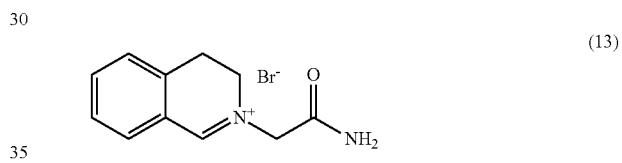

(13)

2 g (15 mmol) of 3,4-dihydroisoquinoline are dissolved under argon in 15 mL of toluene. 8.414 g (61 mmol) of bromoacetamide are added and the mixture is stirred and heated at a temperature of 60° C. for 13 hours. Once the reaction medium has cooled to room temperature, it is filtered. The powder is washed with acetonitrile at room temperature and then at reflux. 3 g of compound 13 are obtained in a yield of 73%.

The NMR and mass analyses are in accordance with the expected structure.

Examples of Compositions and Evaluation

In this example, the effect of improving the oxidizing power afforded by the dihydroisoquinolinium salts according to the invention is studied.

1. Compositions Tested

The compositions used in this example have been obtained from the following ingredients (the percentages indicated are percentages by weight relative to the total weight of the composition).

Preparation of Composition A:

| Composition A | |
|---|---|
| 2-Octyldodecanol | 11.5 |
| Liquid petroleum jelly | 74.5 |
| Oxyethylenated (2 OE) lauryl alcohol | 3 |
| Oxyethylenated (4 OE) sorbitan monolaurate | 11 |

Preparation of the Oxidizing Composition B:

| Oxidizing composition B | |
| --- | --- |
| Glycerol | 0.5 |
| (50% linear 70/30 $C_{13}/C_{15}$)alkyl ether carboxylic acid monoethanolamide (2 OE) | 0.85 |
| Tetrasodium pyrophosphate decahydrate | 0.02 |
| 50% hydrogen peroxide solution (200-volume aqueous hydrogen peroxide solution) | 12 |
| Disodium tin hexahydroxide | 0.04 |
| Diethylenetriaminepentaacetic acid, pentasodium salt as an aqueous 40% solution | 0.15 |
| Cetylstearyl alcohol/oxyethylenated (30 OE) cetylstearyl alcohol mixture | 2.85 |
| Water | qs 100 |

Preparation of Compositions 1 to 5:

Compositions 1 to 5 below were prepared by mixing 1 g of composition A, 1.5 g of the oxidizing composition B and by adding the dyes synthesized above (compounds 1, 2, 3 and 13).

| | Composition 1 | Composition 2 | Composition 3 | Composition 4 | Composition 5 |
| --- | --- | --- | --- | --- | --- |
| 2-(3-imidazol-1-ylpropyl)-3,4-dihydroisoquinolinium bromide (1) | — | 30 mg | — | — | — |
| 2-[3-(3-methyl-1H-imidazol-3-ium-1-yl)propyl]-3,4-dihydroisoquinolinium bromide 4-methylbenzenesulfonate (2) | — | — | 30 mg | — | — |
| 2-(4-bromobutyl)-3,4-dihydroisoquinolinium bromide (3) | — | — | — | 30 mg | — |
| 2-carbamoylmethyl-3,4-dihydroisoquinolinium bromide (13) | — | — | — | — | 30 mg |
| Formula A | 1 g | 1 g | 1 g | 1 g | 1 g |
| Oxidizing formula B ($H_2O_2$) | 1.5 g | 1.5 g | 1.5 g | 1.5 g | 1.5 g |
| Aqueous ammonia 20% $NH_4OH$ | pH = 9.5 | pH = 9.5 | pH = 9.5 | pH = 9.5 | pH = 9.5 |

II. Procedure

The following procedure is applied for each composition described in the preceding table.

After preparation, compositions 1 to 5 are applied to natural 250 mg locks with a tone depth of 4. After a leave-on time of 30 minutes at a temperature of 27° C., the locks are washed, shampooed and dried.

The lightening is measured via the lightness (L*) using a Minolta CM-3610d spectrophotometer:

III. Results

The results are summarized below:

| | Composition 1 | Composition 2 | Composition 3 | Composition 4 | Composition 5 |
| --- | --- | --- | --- | --- | --- |
| Lightness (L*) | 24.4 | 28.0 | 32.2 | 27.0 | 25.5 |

It is noted that greater lightening is obtained with compositions 2 to 5 according to the invention than with composition 1.

In particular, it is noted that the presence of the particular dihydroisoquinolinium salts makes it possible to improve the oxidizing power of hydrogen peroxide and thus to boost its activity (comparison between composition 1 and compositions 2 to 5).

2. Compositions Tested

Composition (A) and oxidizing composition (B) have been prepared from the following ingredients (the percentages indicated are percentages by weight relative to the total weight of the composition).

Composition (A):

| 2-Octyldodecanol | 11.5 |
| --- | --- |
| Laureth-2 | 3 |
| Polysorbate 21 | 11 |
| Mineral oil/Paraffinum liquidum | 74.5 |

Oxidizing Composition (B):

| GLYCERIN | 0.5 |
| --- | --- |
| TRIDECETH-2 CARBOXAMIDE MEA | 0.85 |
| TETRASODIUM PYROPHOSPHATE | 0.02 |
| HYDROGEN PEROXIDE (50%) | 12 |
| SODIUM STANNATE | 0.04 |
| PENTASODIUM PENTETATE (40% in water) | 0.15 |
| CETEARYL ALCOHOL/CETEARETH-25 (80/20) | 2.85 |
| WATER | Qsp 100 |

Compositions 6 (comparative) and 7 (invention) below were prepared by mixing 1 g of composition A, 1.5 g of the oxidizing composition B and by adding dihydroisoquinolinium dyes to be compared.

| | Composition 6 (comparative) | Composition 7 (invention) |
| --- | --- | --- |
| | 30 mg | — |

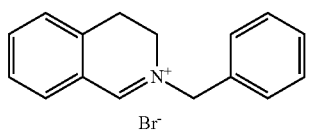 [SMILES: C1=[N+](Cc2ccccc2)CCc2ccccc21 ; [Br-]]

2-benzyl-3,4-dihydroisoquinolinium bromide

|  | Composition 6 (comparative) | Composition 7 (invention) |
|---|---|---|
| 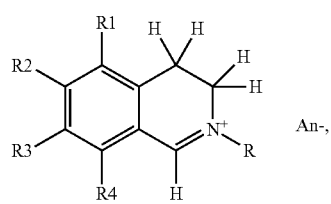<br>2-[3-(3-methyl-1H-imidazol-3-ium-1-yl)propyl]-3,4-dihydroisoquinolinium bromide 4-methylbenzenesulfonate |  | 30 mg |
| Composition (A) | 1 g | 1 g |
| Oxidizing composition (B) | 1.5 g | 1.5 g |
| Aqueous ammonia 20% NH$_4$OH | qs pH = 9.5 | qs pH = 9.5 |

II. Procedure

After preparation, compositions 6 and 7 are applied to natural 250 mg locks with a tone depth of 4. After a leave-on time of 30 minutes at a temperature of 27° C., the locks are washed, shampooed and dried.

The lightening is measured using the CIE L*a*b* system with a Minolta CM-3610d Spectrophotometer (illuminant D65, angle 10°, specular component included). According to this system, L* indicates the lightness of the hair.

The lightening is represented by the L*value: the higher the L* is, the better the lightening is.

III. Results

The results are summarized below:

|  | Composition 6 comparative | Composition 7 Invention |
|---|---|---|
| Lightness (L*) | 28.7 | 36.1 |

The results show that composition 7 according to the invention exhibits a better lightening than composition 6 (comparative).

The invention claimed is:

1. A method for treating keratin materials, the method comprising applying to the keratin materials at least one compound of formula (I), addition salts thereof, or solvates thereof:

(I)

wherein in formula (I):
R represents a linear or branched $C_1$-$C_{20}$ alkyl radical, substituted with a group chosen from:
an amino group —NR$_7$R$_8$,
a cyano group,
a halogen atom,
an aminocarbonyl group —CONH$_2$,
a ($C_1$-$C_6$)alkoxycarbonyl group,
a saturated or unsaturated, optionally aromatic, 5- or 6-membered cationic heterocycle optionally substituted with at least one radical, which may be identical or different, chosen from a linear or branched $C_1$-$C_6$ alkyl radical, a $C_1$-$C_6$ hydroxyalkyl radical, a $C_1$-$C_6$ alkoxy radical, a hydroxyl radical, or an amino radical —NR$_5$R$_6$; or
an ammonium radical N$^+$R$_a$R$_b$R$_c$ wherein R$_a$, R$_b$, and R$_c$ are chosen from, independently of each other, a linear or branched $C_1$-$C_6$ alkyl radical or a $C_1$-$C_6$ hydroxyalkyl radical,
with the proviso that when R represents an alkyl radical substituted with a cationic group, then the electrical neutrality of the compounds of formula (I) is ensured by the presence of at least one cosmetically acceptable anion X$^-$, X$^-$ adding to the anion An$^-$,
R$_1$, R$_2$, R$_3$, and R$_4$ represent, independently of each other, a radical chosen from:
a hydrogen atom,
a linear or branched $C_1$-$C_6$ alkyl radical optionally substituted with at least one group, which may be identical or different, chosen from hydroxyl, $C_1$-$C_6$ alkoxy or amino —NR$_5$R$_6$ groups,
a hydroxyl radical,
an amino radical —NR$_5$R$_6$,
a $C_1$-$C_6$ alkoxy radical;
an aminocarbonyl radical —CONH$_2$, or
a carboxyl radical —COOH,
R$_5$ and R$_6$, which may be identical or different, are chosen from a hydrogen atom or a linear or branched $C_1$-$C_6$ alkyl radical,
R$_7$ and R$_8$, which may be identical or different, are chosen from a linear or branched $C_1$-$C_6$ alkyl radical, substituted with a hydroxyl group, and
An$^-$ and X$^-$ representing, independently of each other, a cosmetically acceptable anion or mixture of anions which ensures the electrical neutrality of the compounds of formula (I).

2. The method according to claim 1, wherein R$_1$, R$_2$, R$_3$, and R$_4$ are identical.

3. The method according to claim 1, wherein R$_1$, R$_2$, R$_3$ and R$_4$ each represent a hydrogen atom.

4. The method according to claim 1, wherein R is chosen from a linear $C_1$-$C_6$ alkyl radical or a linear $C_1$-$C_4$ alkyl radical.

5. The method according to claim 1, wherein the at least one compound of formula (I) is chosen from the compounds of formula (II), addition salts thereof, solvates thereof, or hydrates thereof:

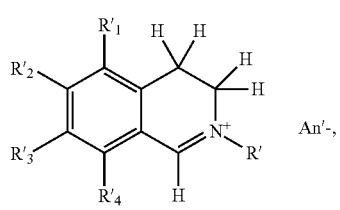

wherein in formula (II):
R' represents a linear or branched $C_1$-$C_{20}$ alkyl radical, substituted with a group chosen from:
a group —NR$_7$R$_8$,
a cyano group,
a halogen atom,
an aminocarbonyl group —CONH$_2$,
a ($C_2$-$C_6$)alkoxycarbonyl group,
a saturated or unsaturated, optionally aromatic, 5- or 6-membered cationic heterocycle, optionally substituted with at least one radical, which may be identical or different, chosen from:
a linear or branched $C_1$-$C_6$ alkyl radical,
a $C_1$-$C_6$ hydroxyalkyl radical,
a $C_1$-$C_6$ alkoxy radical,
a hydroxyl radical, or
an amino radical —NR$_5$R$_6$, or
an ammonium radical N$^+$R$_a$R$_b$R$_c$ wherein R$_a$, R$_b$, and R$_c$, independently of each other, are chosen from a linear or branched $C_1$-$C_6$ alkyl radical or a $C_1$-$C_6$ hydroxyalkyl radical,
with the proviso that when R' represents an alkyl radical substituted with a cationic group, then the electrical neutrality of the compounds of formula (I) is ensured by the presence of at least one cosmetically acceptable anion X$^-$, X$^-$ adding to the anion An$^-$,
R'$_1$, R'$_2$, R'$_3$, and R'$_4$ represent, independently of each other, a radical chosen from:
a hydrogen atom,
a linear or branched $C_1$-$C_6$ alkyl radical optionally substituted with at least one group, which may be identical or different, chosen from hydroxyl, $C_1$-$C_6$ alkoxy or amino —NR$_5$R$_6$ groups,
an amino radical —NR$_5$R$_6$,
an amino radical —NH$_2$,
an aminocarbonyl radical —CONH$_2$, or
a carboxyl radical —COOH,
R$_7$ and R$_8$, which may be identical or different, represent a linear or branched $C_1$-$C_6$ alkyl radical, substituted with a hydroxyl group,
R$_5$ and R$_6$, which may be identical or different, represent a linear or branched $C_1$-$C_6$ alkyl radical; and
An'$^-$ and X$^-$ representing, independently of each other, a cosmetically acceptable anion or mixture of anions which ensures the electrical neutrality of the compounds of formula (II).

6. The method according to claim 5, wherein R' represents a linear $C_1$-$C_6$ alkyl radical substituted with:
a cyano group,
a halogen atom,
a ($C_2$-$C_6$)alkoxycarbonyl group,
a saturated or unsaturated, optionally aromatic, 5- or 6-membered cationic heterocycle chosen from the following formulae:

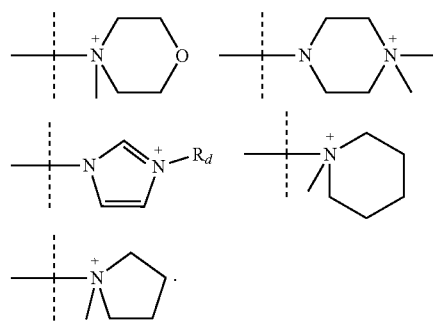

with R$_d$ corresponding to a linear $C_1$-$C_4$ alkyl radical, or
an ammonium radical N$^+$R$_a$R$_b$R$_c$, wherein R$_a$, R$_b$, and R$_c$, independently of each other, are chosen from a $C_1$-$C_3$ alkyl radical.

7. The method according to claim 1, wherein the at least one compound of formula (I) is chosen from the following compounds:

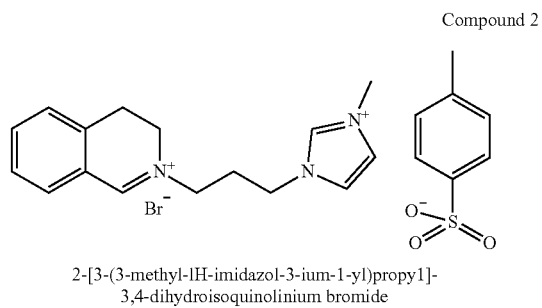

Compound 2

2-[3-(3-methyl-1H-imidazol-3-ium-1-yl)propyl]-3,4-dihydroisoquinolinium bromide 4-methylbenzenesulfonate

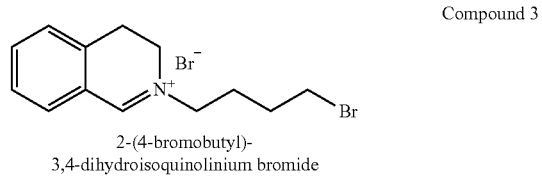

Compound 3

2-(4-bromobutyl)-3,4-dihydroisoquinolinium bromide

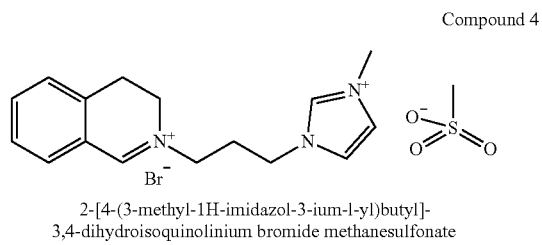

Compound 4

2-[4-(3-methyl-1H-imidazol-3-ium-1-yl)butyl]-3,4-dihydroisoquinolinium bromide methanesulfonate Compound 7

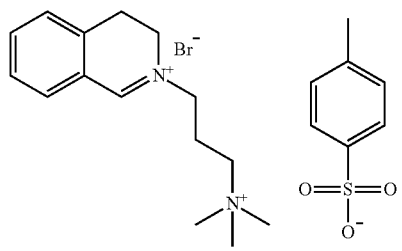

2-[3-(trimethylammonio)propyl]-
3,4-dihydroisoquinolinium bromide
4-methylbenzenesulfonate Compound 8

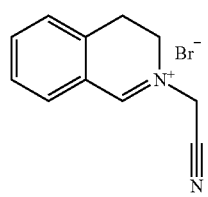

2-cyanomethyl-3,4-dihydroisoquinolinium bromide

Compound 11

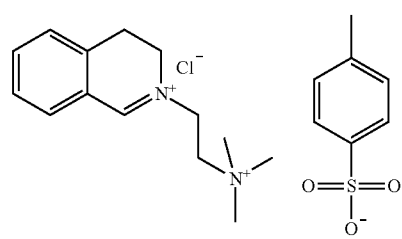

2-[2-(trimethylammonio)ethyl]-
3,4-dihydroisoquinolinium chloride
4-methylbenzenesulfonate Compound 12

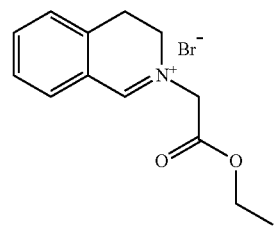

2-ethoxycarbonylmethyl-
3,4-dihydroisoquinolinium bromide

Compound 13

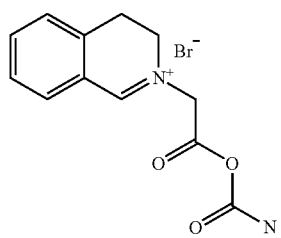

2-carbamoylmethyl-
3,4-dihydroisoquinolinium bromide

Compound 15

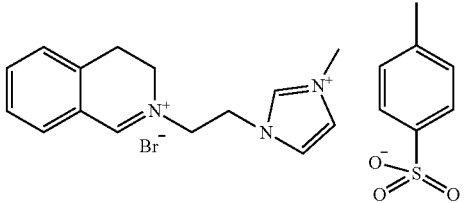

2-[3-(3-methyl-1H-imidazol-3-ium-1-yl)ethyl]-
3,4-dihydroisoquinolinium bromide
4-methylbenzenesulfonate Compound 17

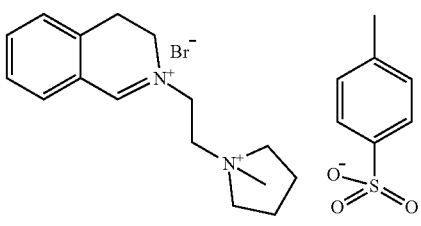

2-[2-(1-methylpyrrolidinium-1-yl)ethyl]-
3,4-dihydroisoquinolinium bromide
4-methylbenzenesulfonate Compound 19

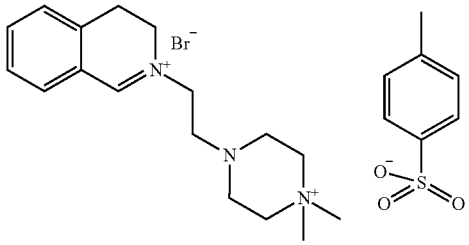

[2-(4,4-di methylpiperazin-4-ium-l-yl)ethyl]-
3,4-dihydroisoquinolinium bromide
4-methylbenzenesulfonate Compound 20

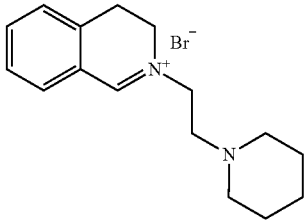

2-(2-piperidin-1-ylethyl)-
3,4-dihydroisoquinolinium bromide

Compound 21

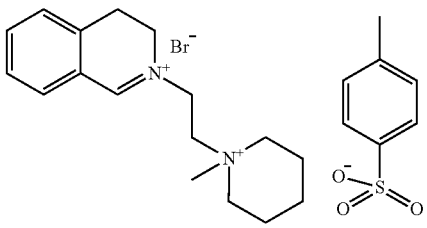

2-[2-(1-methylpiperidinium-1-yl)ethyl]-
3,4-dihydroisoquinolinium bromide
4-methylbenzenesulfonate Compound 23

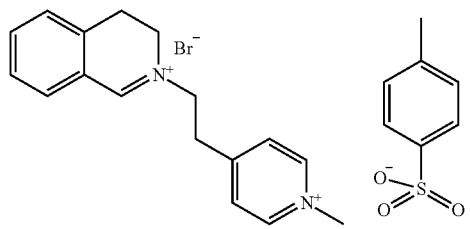

2-[2-(1-methylpyridinium-4-yl)ethyl]-
3,4-dihydroisoquinolinium bromide
4-methylbenzenesulfonate Compound 25

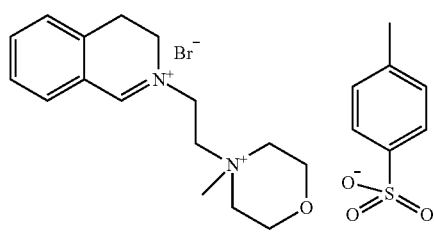

2-[2-(4-methylmorpholin-4-ium-4-yl)ethyl]-
3,4-dihydroisoquinolinium bromide
4-methylbenzenesulfonate Compound 27

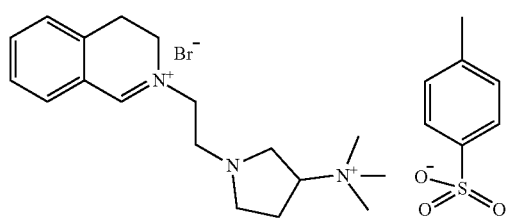

2-{2-[3-trimethylammonio)pyrrolidin-1-yl]ethyl}-
3,4- dihydroisoquinolinium bromide
4-methylbenzenesulfonate or mixtures thereof.

8. A method for improving the oxidizing activity of at least one chemical oxidizing agent, the method comprising combining at least one compound of formula (I), addition salts thereof, or solvates thereof in the presence of at least one chemical oxidizing agent:

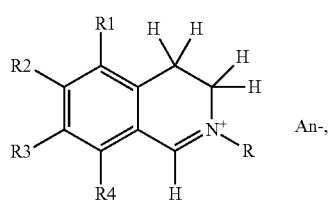

(I)

wherein in formula (I):
R represents a linear or branched $C_1$-$C_{20}$ alkyl radical, substituted with a group chosen from:
an amino group —$NR_7R_8$,
a cyano group,
a halogen atom,
an aminocarbonyl group —$CONH_2$,
a ($C_1$-$C_6$)alkoxycarbonyl group,
a saturated or unsaturated, optionally aromatic, 5- or 6-membered cationic heterocycle optionally substituted with at least one radical, which may be identical or different, chosen from a linear or branched $C_1$-$C_6$ alkyl radical, a $C_1$-$C_6$ hydroxyalkyl radical, a $C_1$-$C_6$ alkoxy radical, a hydroxyl radical, or an amino radical —$NR_5R_6$; or
an ammonium radical $N^+R_aR_bR_c$ wherein $R_a$, $R_b$, and $R_c$ are chosen from, independently of each other, a linear or branched $C_1$-$C_6$ alkyl radical or a $C_1$-$C_6$ hydroxyalkyl radical,
with the proviso that when R represents an alkyl radical substituted with a cationic group, then the electrical neutrality of the compounds of formula (I) is ensured by the presence of at least one cosmetically acceptable anion $X^-$, $X^-$ adding to the anion $An^-$,
$R_1$, $R_2$, $R_3$, and $R_4$ represent, independently of each other, a radical chosen from:
a hydrogen atom,
a linear or branched $C_1$-$C_6$ alkyl radical optionally substituted with at least one group, which may be identical or different, chosen from hydroxyl, $C_1$-$C_6$ alkoxy or amino —$NR_5R_6$ groups,
a hydroxyl radical,
an amino radical —$NR_5R_6$,
a $C_1$-$C_6$ alkoxy radical;
an aminocarbonyl radical —$CONH_2$, or
a carboxyl radical —COOH,
$R_5$ and $R_6$, which may be identical or different, are chosen from a hydrogen atom or a linear or branched $C_1$-$C_6$ alkyl radical,
$R_7$ and $R_8$, which may be identical or different, are chosen from a linear or branched $C_1$-$C_6$ alkyl radical, substituted with a hydroxyl group, and
$An^-$ and $X^-$ representing, independently of each other, a cosmetically acceptable anion or mixture of anions which ensures the electrical neutrality of the compounds of formula (I).

9. The method according to claim 1, for the lightening of keratin materials.

10. The method according to claim 1, wherein the applying of at least one compound of formula (I), addition salts thereof, or solvates thereof, occurs in the presence of at least one chemical oxidizing agent chosen from hydrogen peroxide, urea peroxide, alkali metal bromates, persalts, perborates, persulfates, peracids, oxidase enzymes, peroxidases, two-electron oxidoreductases, uricases, four-electron oxygenases, laccases, or a combination thereof.

11. The method according to claim 1, wherein R represents a linear or branched $C_1$-$C_{20}$ alkyl radical, substituted with a group chosen from a saturated or unsaturated, optionally aromatic, 5- or 6-membered cationic heterocycle optionally substituted with at least one radical, which may be identical or different, chosen from a linear or branched $C_1$-$C_6$ alkyl radical, a $C_1$-$C_6$ hydroxyalkyl radical, a $C_1$-$C_6$ alkoxy radical, a hydroxyl radical, or an amino radical —$NR_5R_6$; $R_5$ and $R_6$, which may be identical or different, are chosen from a hydrogen atom or a linear or branched $C_1$-$C_6$ alkyl radical.

* * * * *

UNITED STATES PATENT AND TRADEMARK OFFICE
CERTIFICATE OF CORRECTION

PATENT NO. : 11,406,580 B2
APPLICATION NO. : 16/064256
DATED : August 9, 2022
INVENTOR(S) : Sabelle et al.

Page 1 of 1

It is certified that error appears in the above-identified patent and that said Letters Patent is hereby corrected as shown below:

In the Claims

Claim 7, Column 31, Lines 61-63, please remove Compound 13 and insert the following:

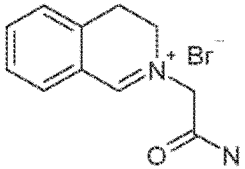

| | 2-carbamoylmethyl-3,4-dihydroisoquinolinium bromide Compound 13 |

Signed and Sealed this
Twenty-third Day of May, 2023

Katherine Kelly Vidal
*Director of the United States Patent and Trademark Office*